(12) United States Patent
Oka et al.

(10) Patent No.: US 6,611,611 B2
(45) Date of Patent: Aug. 26, 2003

(54) PARTICLE SENSOR

(75) Inventors: Shoichi Oka, Matsuzaka (JP);
Masanori Hayashi, Kadoma (JP);
Shinji Kirihata, Kyoto (JP); Takayuki Nishikawa, Osaka (JP); Koji Sakamoto, Takarazuka (JP); Takeshi Wada, Tsu (JP)

(73) Assignee: Matsushita Electric Works, Ltd., Kadoma (JP)

( * ) Notice: Subject to any disclaimer, the term of this patent is extended or adjusted under 35 U.S.C. 154(b) by 0 days.

(21) Appl. No.: 09/926,635

(22) PCT Filed: May 28, 2001

(86) PCT No.: PCT/JP01/02539
§ 371 (c)(1),
(2), (4) Date: Nov. 28, 2001

(87) PCT Pub. No.: WO01/73381
PCT Pub. Date: Oct. 4, 2001

(65) Prior Publication Data
US 2002/0135764 A1 Sep. 26, 2002

(30) Foreign Application Priority Data
Mar. 28, 2000 (JP) .......................................... 2000-88760

(51) Int. Cl.[7] .................................................. G06K 9/00
(52) U.S. Cl. ...................................... 382/110; 356/335
(58) Field of Search ........................ 382/100, 141–145, 382/312–325; 356/335–336

(56) References Cited

U.S. PATENT DOCUMENTS

| 4,830,494 A | * | 5/1989 | Ishikawa et al. ............ 356/336 |
| 5,867,514 A | | 2/1999 | Anderson |
| 6,501,325 B1 | * | 12/2002 | Meng ........................... 327/536 |
| 6,529,619 B2 | * | 3/2003 | Ishikawa et al. ............ 382/141 |

FOREIGN PATENT DOCUMENTS

| EP | 0 297 818 | 1/1989 |
| EP | 0 821 476 | 1/1998 |
| GB | 2 136 561 | 9/1984 |

* cited by examiner

*Primary Examiner*—Jingge Wu
(74) *Attorney, Agent, or Firm*—Oblon, Spivak, McClelland, Maier & Neustadt, P.C.

(57) ABSTRACT

A particle sensor has a gain control and an offset voltage adjustment so as to provide a consistent sensor output indicative of the particle density in match with a predetermined relationship between the sensor output and the particle density, while compensating for background noises. The gain control and the offset voltage adjustment are realized respectively by digitally controllable variable resistor networks each having a plurality of switches. A memory module is included in the sensor to store instruction data for control of the switches and therefore responsible for the gain control and the offset voltage adjustment. In particular, the particle sensor includes a memory interface which enables the selective use of two types of memory means, one is an intelligent memory module composed of EEPROM and a microcomputer, and the other is a normal memory module consisting of EEPROM.

11 Claims, 7 Drawing Sheets

PARTICLE SENSOR

TECHNICAL FIELD

The present invention relates to a particle sensor for detecting smoke particles or the like, and more particularly to such a particle sensor having an output adjustment capability.

BACKGROUND ART

Particle sensors have been widely utilized in the art for monitoring the amount of particles such as smoke particles in an environment in order to determine the criticality level of the particle density. The particle sensor is normally designed to include a photo-detector which provides an output voltage proportional to the amount of the particles carried on the air being monitored. A light emitter is utilized in association with the photo-detector to project a light beam into a detection chamber for giving the scattered light due to the presence of the particles in the chamber. It is this scattered light that is collected by the photo-detector which, in turn, provides the output voltage indicative of the amount of the particles present in the chamber. A gain of the output voltage is then processed in order to satisfy a predetermined or regulation relationship between the output voltage and a particle density. Further, in order to cancel a background noise, i.e., a background voltage such as resulting from a stray light received by the photo-sensor, a suitable offset voltage reflecting the background voltage is combined with the output voltage to give a sensor output truly indicative of the amount or density of the particles. The gain control and the offset voltage are each realized by a mechanical variable resistor. Although the large number of the components forming the sensor can be easily assembled into an integrated circuit of a compact structure, the mechanical variable resistors which are inherently bulky have to be external to the integrated circuit and become hindrance to making the whole sensor structure compact. Also, since the mechanical variable resistors are external to the integrated circuit, they may become sources of noise for the integrated circuit, lowering reliability of the detector. Further, the mechanical variable resistor is not suitable for remote control adjustment of resistance because of the remote control adjustment requires a complicated means of processing visual image of an adjustor dial of the mechanical variable resistor to estimate a current resistance and further actuating the adjustor dial.

DISCLOSURE OF THE INVENTION

The present invention has been accomplished in view of the above problems to provide a particle sensor which is compact, reliable in operation, and easy for adjustment. The particle sensor in accordance with the present invention comprises a detector proving an output voltage which is proportional to the amount of particles carried on a medium such as the air being detected, a gain controller adjusting the output voltage received from the detector to provide an adjusted output voltage, and an offset voltage adjustor providing an adjustable offset voltage indicative of a background voltage or noise. The offset voltage is combined with the adjusted output voltage to provide a sensor output which. satisfies a predetermined relationship between particle density and the sensor output. The gain controller includes a gain resistor network which gives a variable resistance in order to vary the adjusted output voltage, and the offset voltage adjustor includes an offset resistor network which gives a variable resistance in order to adjust the offset voltage. Either one or both of the gain resistor network and the offset resistor network comprise a plurality of digitally controllable switches and a plurality of resistors so as to give the variable resistance varying by conduction of a suitable combination of the switches. Also included in the sensor is a memory module which stores an instruction data designating which one or more of the switches are to be made conductive, and a memory interface which transfers the instruction data from the memory module to at least one of the gain resistor network and the offset resistor network. With this arrangement, the gain resistor network and the offset resistor network can be assembled together with the gain controller and the offset voltage adjustor into a single compact integrated structure. Thus, the whole sensor can be made compact and be assembled by a reduced number of parts to lower a manufacturing cost. Also with the inclusion of the resistor networks in the integrated circuit, they can be less susceptible to an external noise so as to make the sensor reliable. Further, since the resistor networks is realized as a digitally adjustable resistor network, adjustment of the resistance can be made easy simply by electronically varying the instruction data.

The memory module utilized in the present invention includes a normal type which consist of a non-volatile memory such as EEPROM for storing the instruction data, and an intelligent type composed of a like non-volatile memory storing the instruction data and a microcomputer capable of writing the instruction data. In order to make the particle sensor compatible with the two types of the memory modules, the memory interface is designed to have a memory controller and a selector. The memory controller sends a first clock signal and read signal for reading the instruction data directly from the non-volatile memory in accordance with the first clock signal and transferring the instruction data to the resistor networks. The selector is configured to have inputs respectively adapted to receive the first clock signal from the memory controller and a second clock signal, and to select one of the first and second clock signals. The second clock signal is supplied from other than the memory controller, i.e., from the microcomputer and is utilized to read the instruction data from the non-volatile memory under the control of the microcomputer and to transfer the instruction data to the resistor networks. Thus, the sensor can operate with either of two types of the memory modules simply by selecting the clock signal at the selector, which is therefore another object of the present invention.

In this connection, the memory interface may include a shift-register which receives the instruction data from the non-volatile memory either by way of the microcomputer or directly from the non-volatile memory, and transfers the instruction data to the resistor networks. The shift-register is connected to the selector to receive the selected one of the first and second clock signal and is connected to receive the instruction data through a data channel. When the normal memory module is utilized, the data channel is connected to receive the instruction data directly from the memory. For the intelligent memory module, the data channel is connected to the microcomputer to receive the instruction data through the microcomputer. The instruction data is transmitted in accordance with the selected one of the first and second clock signal into the shift-register to be subsequently delivered to the resistor networks. With the use of the shift-register, it is possible to check validity of the instruction data for increased reliability of the sensor output.

When the intelligent memory module is utilized, the instruction data is preferred to have a data structure composed of the following four separate data.

(1) A gain value data having plural bits each designating a conduction state of the corresponding one of the switches included in the gain resistor network, (2) A reverse gain value data having reversed bits of the gain value data;

(3) An offset value data having plural bits each designating a conduction state of the corresponding one of the switches included in the offset resistor network; and (4) A reverse offset value data having reversed bits of the offset value data.

In this connection, the memory interface includes a data validation unit which fetches the instruction data from the shift-register to compare the bits of the gain value data with the corresponding reversed bits, and compare the bits of the offset value data with the corresponding reversed bits in order to verify the gain value data and the offset value data, and provides an error signal when any one of the data is not verified. In response to the error signal, the microcomputer acts to retransmit the instruction data from the memory to the shift-register. Thus, even when the instruction data should become erroneous due to the influence of transient noises, the valid instruction data can replace for the erroneous data to keep providing the reliable sensor output, which is therefore a further object of the present invention.

When the normal memory module is utilized, the memory controller operates to fetch the instruction data periodically from the non-volatile memory for transfer to the resistor networks so as to keep transferring the valid instruction data, thereby ensuring reliable sensor output while avoiding temporary errors which might occur due to transient noises.

Further, the memory interface may include a write interface which accepts a write signal from an external writing device and enables the writing device to write the instruction data in the memory means for facilitating the adjustment of the resistance.

These and still other objects and advantageous features of the present invention will become more apparent from the following description of the embodiments when taken in conjunction with the attached drawings.

MODE FOR CARRYING OUT THE INVENTION

Figure 1:
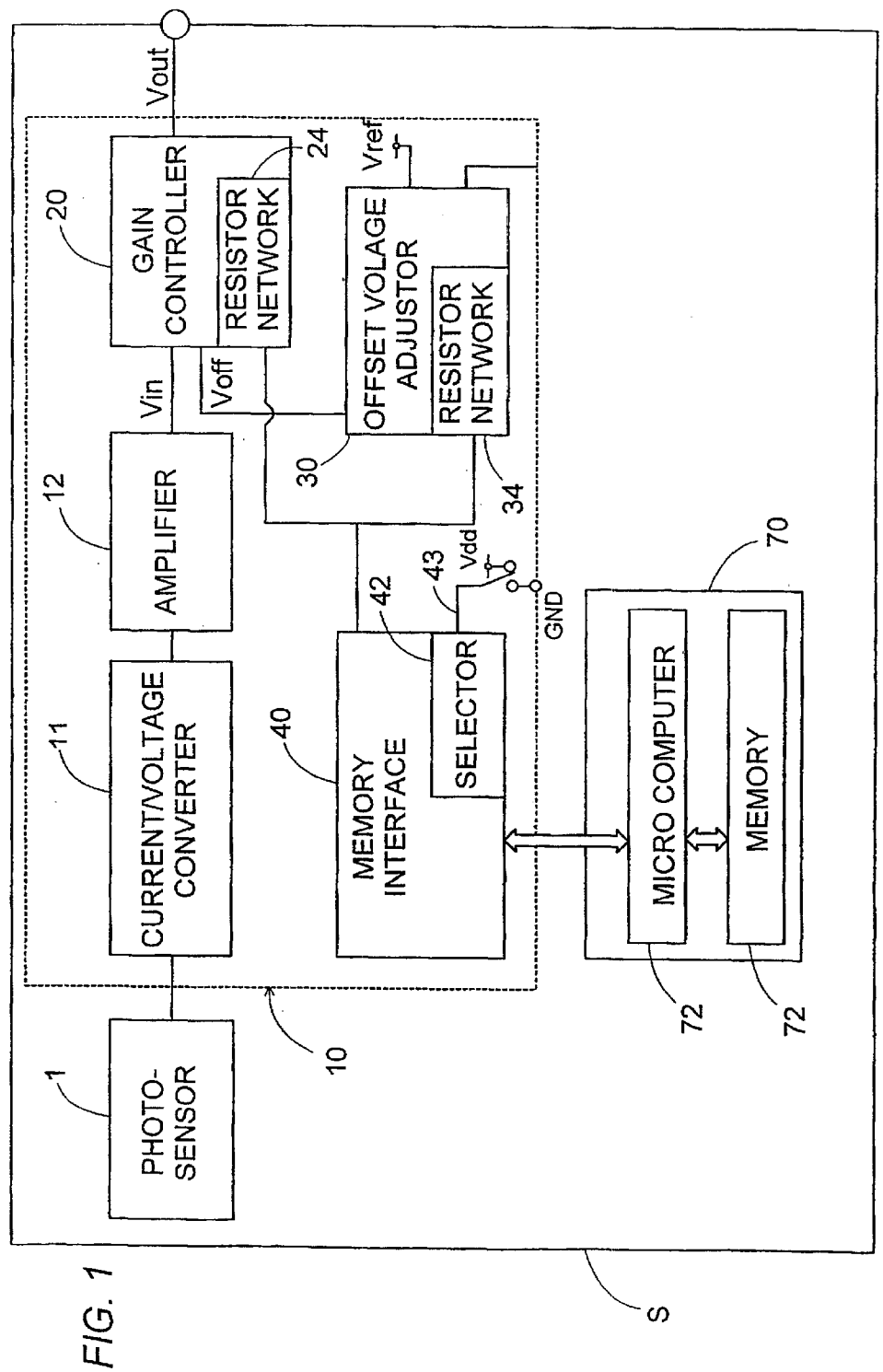
FIG. 1 is a block diagram of a particle sensor in accordance with a first embodiment of the present invention.

A particle sensor in accordance with the present invention is explained in detail. The particle sensor is designed to detect the density of smoke particles or other minute particles such as dust, and is utilized for determination of a fire-presence or dust pollution. As shown in FIG. 1, the particle sensor includes a photo-sensor 1 such as a photo-diode adapted to receive a scattered light resulting from the presence of the particles. That is, the photo-sensor 1 is utilized in combination with a conventional smoke chamber (not shown) entrapping the outside air possibly carrying the smoke particles. The smoke chamber is fitted with a conventional light embitter (also not shown) such as a diode which directs a light beam into the chamber. As the particles are present in the chamber, a corresponding amount of the scattered light is received at the photo-sensor 1 which provides an output current proportional to the amount of the particles in the chamber. The output current is then converted into a voltage at a current-voltage converter 11 and subsequently amplified at an amplifier 12 to give the output voltage indicative of the amount of the particles being detected. In this sense, the photo-sensor 1, the converter 11, and the amplifier 12 are cooperative to define a detector which provides the output voltage as the particle density. The converter 11 and the amplifier 12 are of conventional configuration and are assembled into a single integrated circuit module 10 together with a gain controller 20, an offset voltage adjustor 30, and a memory interface 40.

Figure 6:
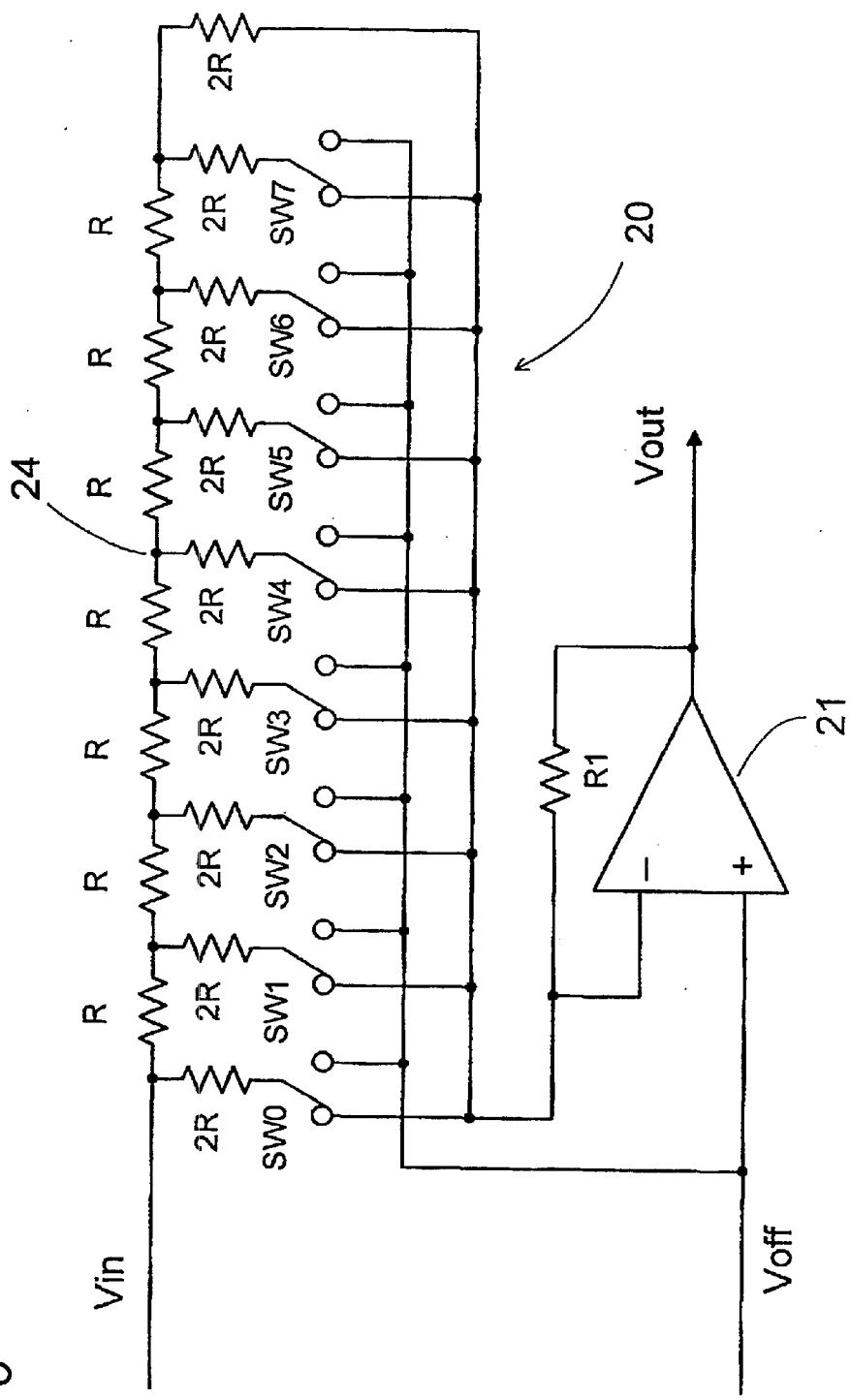
FIGS. 6 and 7 are circuit diagrams respectively showing a gain controller and an offset voltage adjustor utilized in the particle sensor.

The gain controller 20 is included to adjust the output voltage to an increased level, and is composed of an operational amplifier 21 and a resistor network 24, as shown in FIG. 6. The amplifier 21 has an inverted input (−) connected to receive the output voltage Vin through the resistor network 24, and has a non-inverted input (+) to receive an adjustable offset voltage Voff from the offset voltage adjustor 30 so as to give an increased sensor output Vout determined by a resistance of the resistor network 24. The resistor network 24 is a resistor ladder composed of a plurality of resistors R, 2R, R1 and a plurality of switches SW0 to SW7. Each switch is actuated by a digital signal "1" or "0" included in an instruction data supplied to the network from an external memory 71, 81. Thus, any combination of the switches can be made conductive or non-conductive by digital signal to vary the overall resistance of the network, thereby controlling the amplification factor of the amplifier 21, i.e., the gain of the gain controller 20.

Figure 2:
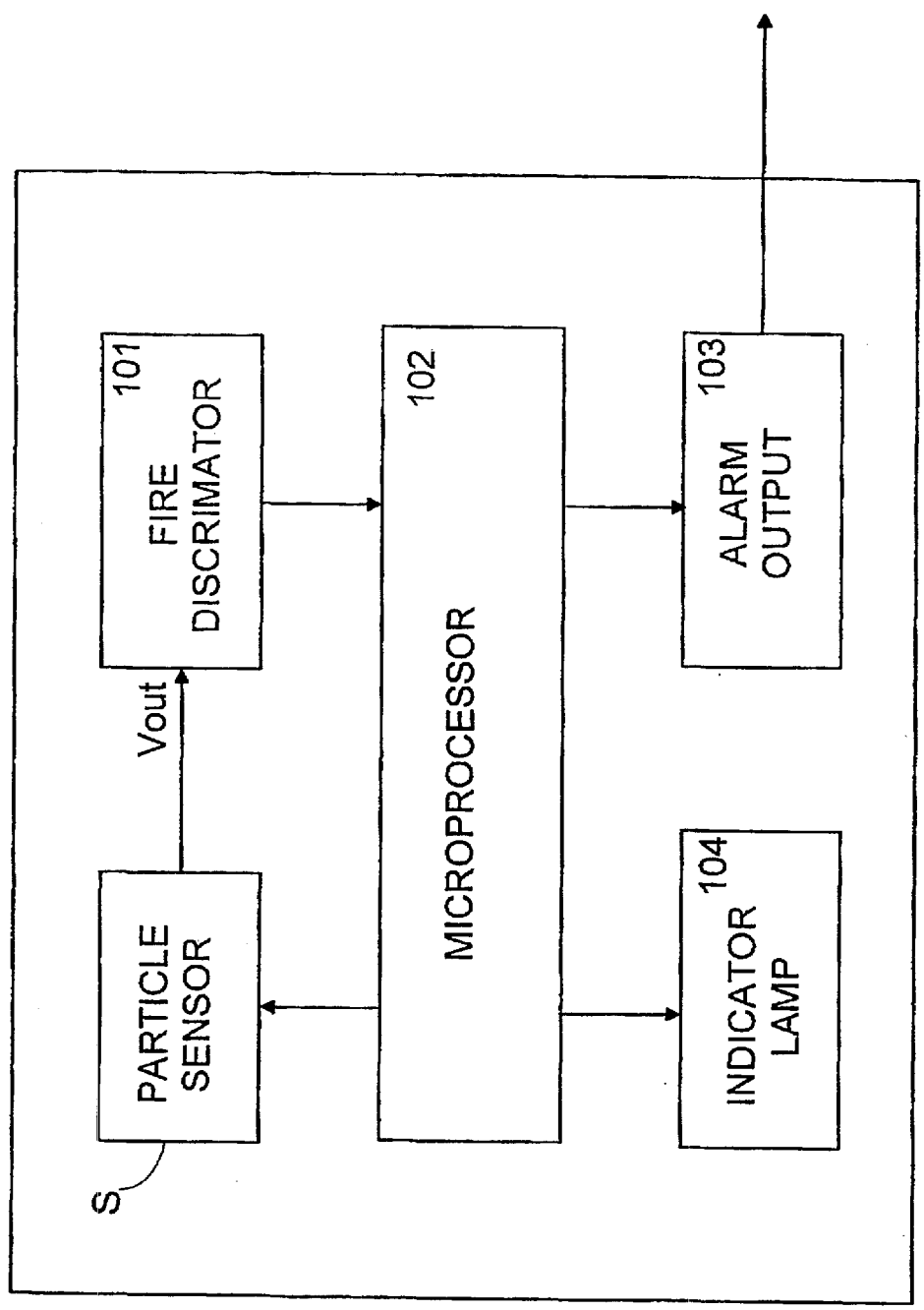
FIG. 2 is a block diagram of a fire alarm device incorporating the particle sensor.
Figure 7:
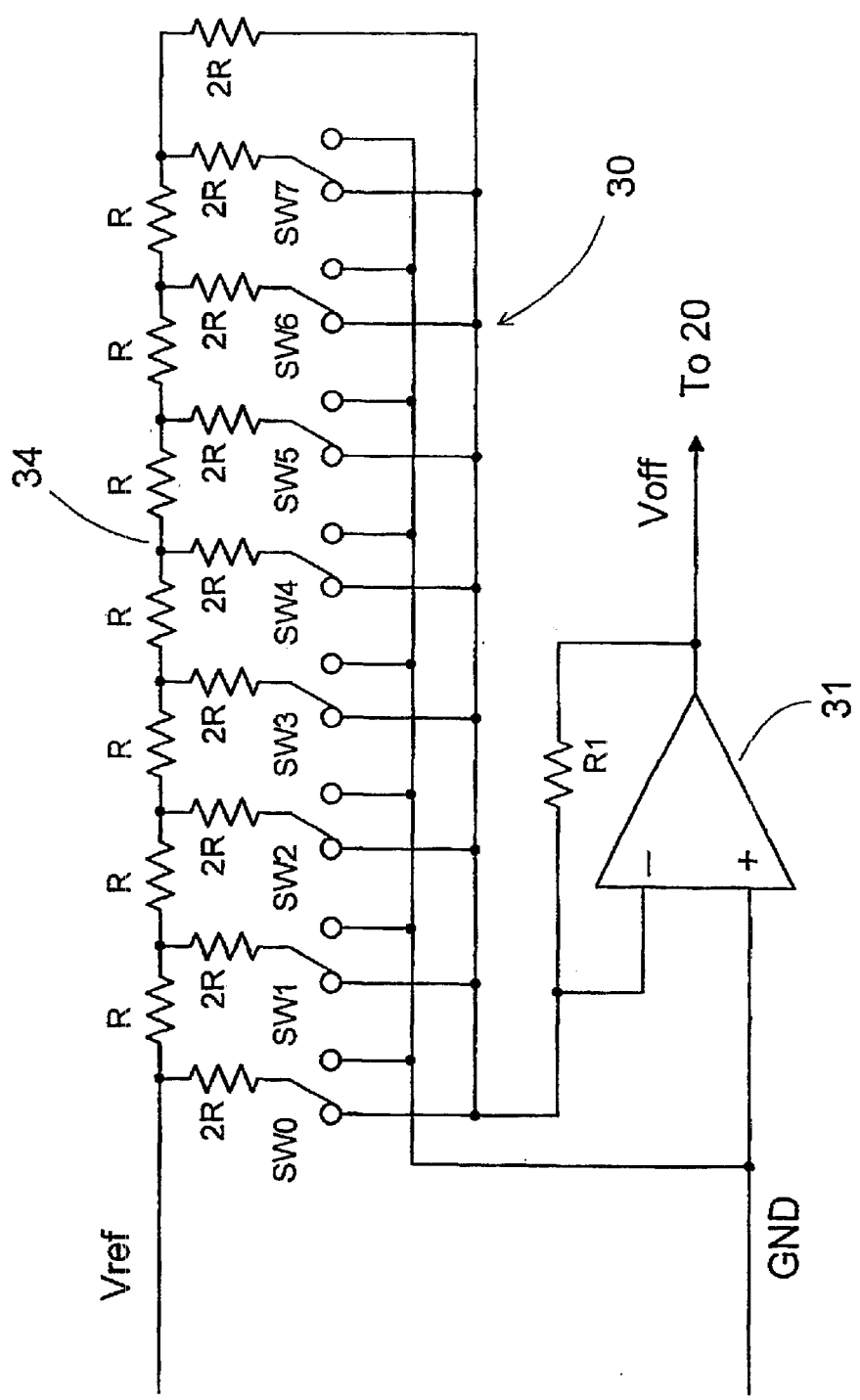

The offset voltage adjustor 30 is provided to give the adjustable offset voltage Voff for indication of a background voltage which reflects a background noise such as resulting from a stray light not due to the presence of the particles. The offset voltage Voff is supplied to the gain controller 20 where it is processed to give the sensor output which satisfies a predetermined or regulation relationship between the sensor output and the density of the particles, thereby giving a standard measure which is utilized for determination of the fire presence based upon the level of the smoke density. One example is shown in FIG. 2, in which the particle sensor S of the present invention is combined with a fire discriminator 101, a microprocessor 102, an alarm output 103, and an indicator lamp 104 to form the fire alarm device. The fire discriminator 101 has a critical level with which the sensor output Vout from the sensor S is compared to judge the presence of the fire. Upon determination of the fire-presence, the microprocessor 102 actuates the alarm output 103 to generate a fire alarm to a supervisor station. The microprocessor 102 also controls the operation of the particle sensor S so as to regularly check the smoke density and send the data thereof to the station. As shown in FIG. 7, the offset voltage is composed of an operational amplifier 31 and a resistor network 34. The amplifier 31 has an inverted input (−) connected to receive a reference voltage Vref through the resistor network 34 and has a non-inverted input (+) to a ground GND so as to give the adjustable offset voltage Voff determined by a resistance of the resistor network 34. The resistor network 34 is a resistor ladder composed of a plurality of resistors R, 2R, R1 and a plurality of switches SW0 to SW7. Each switch is actuated by a digital signal "1" or "0" included in an instruction data supplied to the network from the external memory module 71, 81. Thus, any combination of the switches can be made conductive or non-conductive by the digital signal to vary the overall resistance of the network, thereby adjusting the offset voltage to reflect the background noise, thereby giving the reliable sensor output truly indicative of the particle density being monitored.

Figure 3:
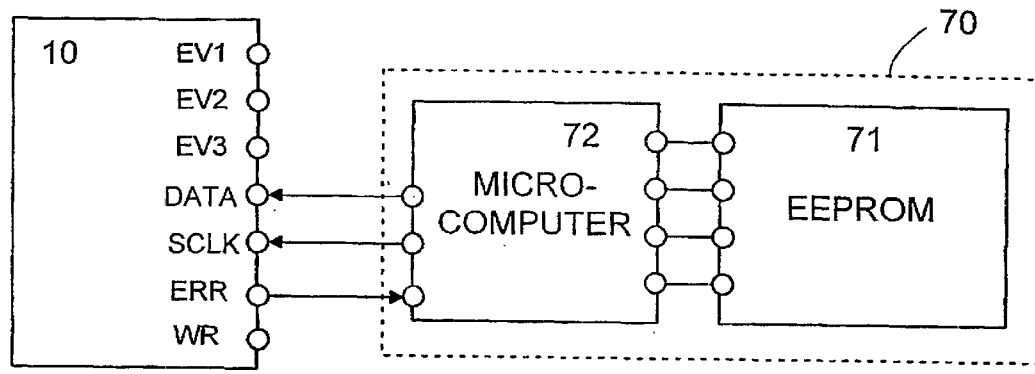
FIG. 3 is a block diagram showing a connection between an integrated circuit forming a major part of the particle sensor and an intelligent type memory module.
Figure 5:
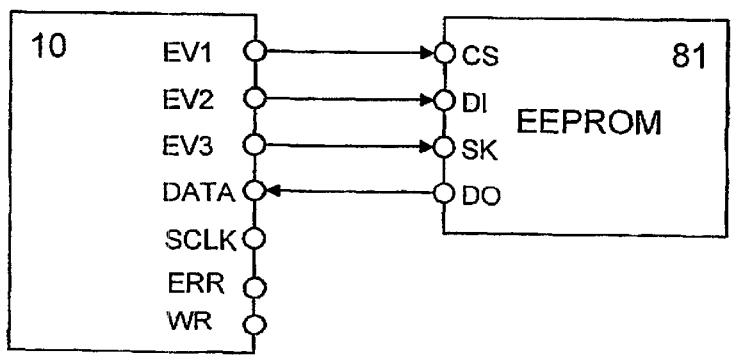
FIG. 5 is a block diagram showing a connection between the integrated circuit and a normal type memory module.
Figure 8:
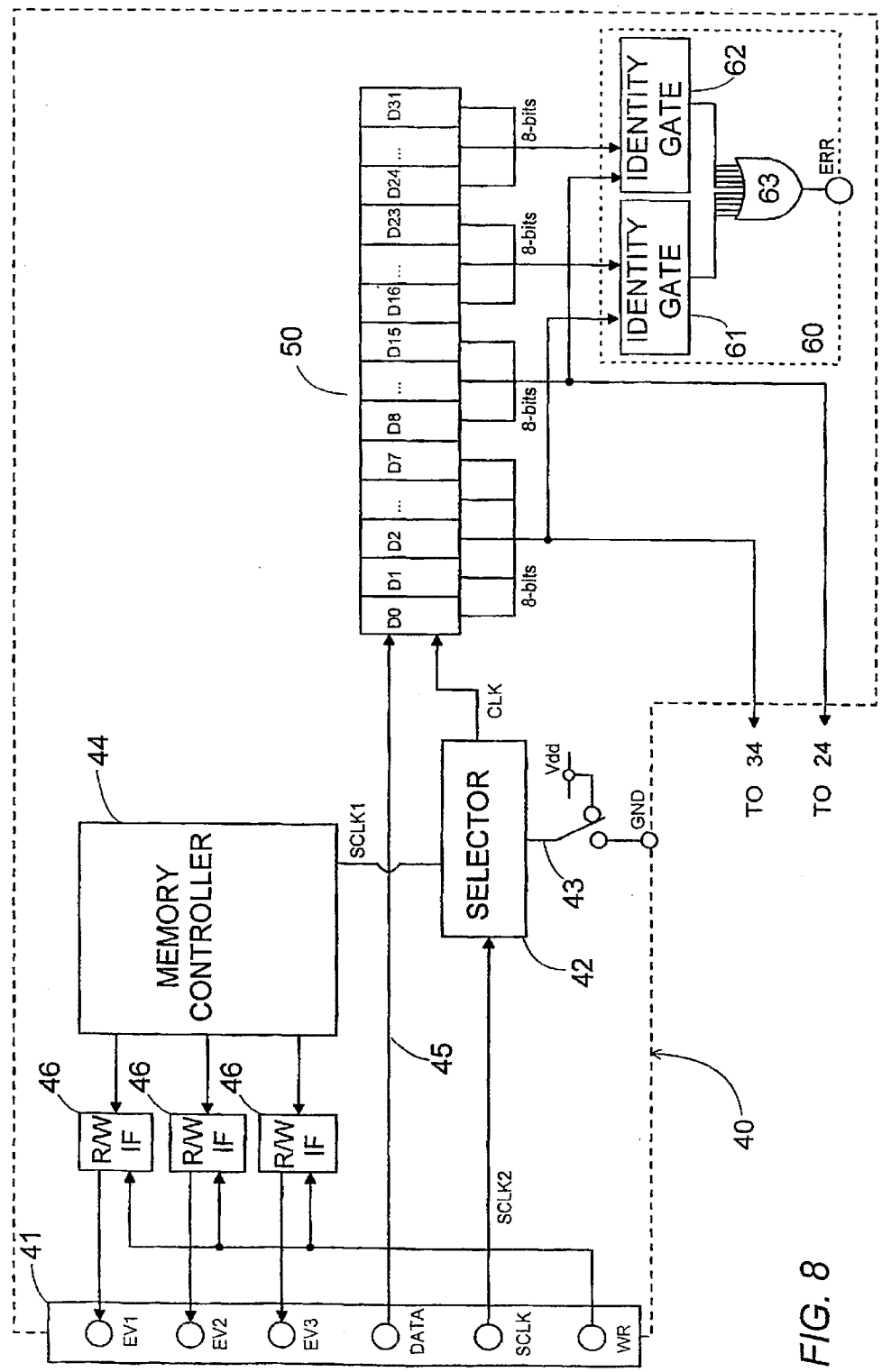
FIG. 8 is a block diagram showing a memory interface incorporated in the particle sensor.

In the present invention, there are provided two types of memory modules which are selectively connected with the memory interface 40 of the integrated circuit module 10. One type is an intelligent memory module 70 composed of the non-volatile memory 71 such as EEPROM storing the instruction data for resistance adjustment of the networks 24 and 34, and a microcomputer 72 capable of reading and writing the instruction data, as shown in FIGS. 1 and 3. The other type is a normal memory module consisting of a like non-volatile memory 81, as shown in FIG. 5. In order to enable the selective use of the memory modules, the memory interface 40 is designed to include a dual-purpose input terminal 41, a selector 42 and a memory controller 44, in addition to a shift-register 50, as shown in FIG. 8. The input terminal 41 has three control terminals EV1, EV2, EV3 for connection to the memory 81, one common data terminal DATA for connection to either one of the memory 81 and the microcomputer 72, and one clock signal input terminal SCLK for connection to the microcomputer 72. That is, the four terminals EV1, EV2, EV3, and DATA are utilized for connection with the normal memory module 81, while the two terminals DATA and SCLK are utilized for connection with the intelligent memory module 70. The selector 42 has two inputs one connected to receive a first clock signal SCLK1 from the memory controller 44, and the other connected to terminal SCLK for receiving a second clock signal SCLK2 utilized in the microcomputer 72 to transfer the instruction data from the associated memory 71. The output of the selector 42 is connected to the shift-register 60 to give the selected clock signal CLK, one of the first and second clock signals SCLKI and SCLK2. For this purpose, the selector 42 has a control terminal 43 which is connected by a jumper pin selectively to a voltage source Vdd and to the ground GND for switching the clock signals. The terminal DATA is connected to the shift-register 50 through a data channel 45.

Figure 4:
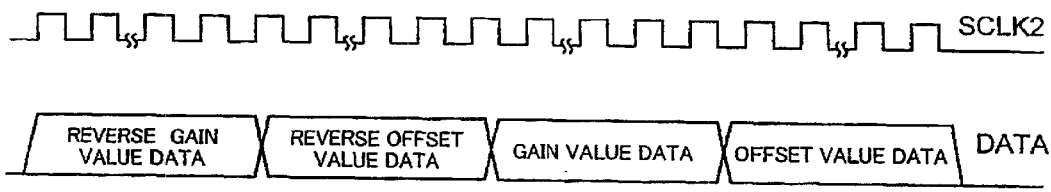
FIG. 4 is a diagram showing a first clock signal and an instruction data transmitted from the intelligent type memory module.

When the intelligent memory module 70 is connected to the integrated circuit module 10, as shown in FIG. 3, the memory controller 44 is deactivated so that the microcomputer 72 takes over to read and transfer the instruction data from the memory 71 to the shift-register 50. The memory controller 44 is connected to the control pin of the selector 42 so as to be deactivated when the selector 42, is set to receive the second clock signal SCLK2. The instruction data stored in the memory 71 of the intelligent memory module 70 has a data structure which, as shown in FIG. 4, is composed of the four separate data.

(1) An offset value data having eight bits such as "01100000" each designating the conduction state of each switch in the offset resistor network;

(2) A gain value data having eight bits such as "01101110" each designating the conduction state of each switch in the gain resistor network, (3) A reverse offset value data having eight bits such as "10011111" reversal bits of the offset value data; and.

(4) A reverse gain value data having eight bits such as "110010001" reversal of the gain value data.

These data are read from the memory 71 and transferred bit-by-bit in the reverse order from the microcomputer 72 to the shift-register 60 in accordance with the second clock signal SCLK2. Thus, after the clock signal SCLK2 stops, the offset value data is stored at D7-D0, the gain value data is at D15-D8, the reverse offset value data at D23-D16, and the reverse gain value data at D31-D24 of the shift-register 50. D07-D0 are connected to the offset resistor network 34 to deliver the offset value data so as to turn on or off the corresponding switches, while D15-D8 are connected to the gain resistor network 24 to deliver the gain value data so as to turn on or off the corresponding switches.

Referring to FIG. 8, the memory interface 40 further includes a data validating unit 60 for validation of the instruction data taken into the shift-register 50 to be delivered to the respective networks 24 and 34 for the gain adjustment as well as the offset voltage adjustment. For this purpose, the validating unit 60 includes a first identity gate 61 which compares every bits of the offset value data with the corresponding reversed bits, and a second identity gate 62 which compares every bits of the gain value data with the corresponding reversed bits. The output of the gates 61 and 62 are connected to an OR gate 63 which provides a high level output as an error signal when there is a discrepancy in any one of the bit couples which indicates that one or more of the data is accidentally modified into erroneous data for some reason, possibly by a transient noise. The error signal is sent through a corresponding output terminal ERR to the microcomputer 72 which responds to retransmit the valid instruction data from the memory 71 to the shift-register 50 to replace for the erroneous data, thereby keeping the consistent adjustment values for reliable detection of the particle density. It is noted in this connection that the microcomputer 72 is given a capability of writing the instruction data of the memory 71. In addition to the writing capability, the microcomputer 72 is given a capability of acknowledging the type of the photo-sensor and selecting, from various sets of the instruction data stored in the memory, a suitable set of the instruction data associated with the acknowledged type of the photo-sensor.

Figure 9:
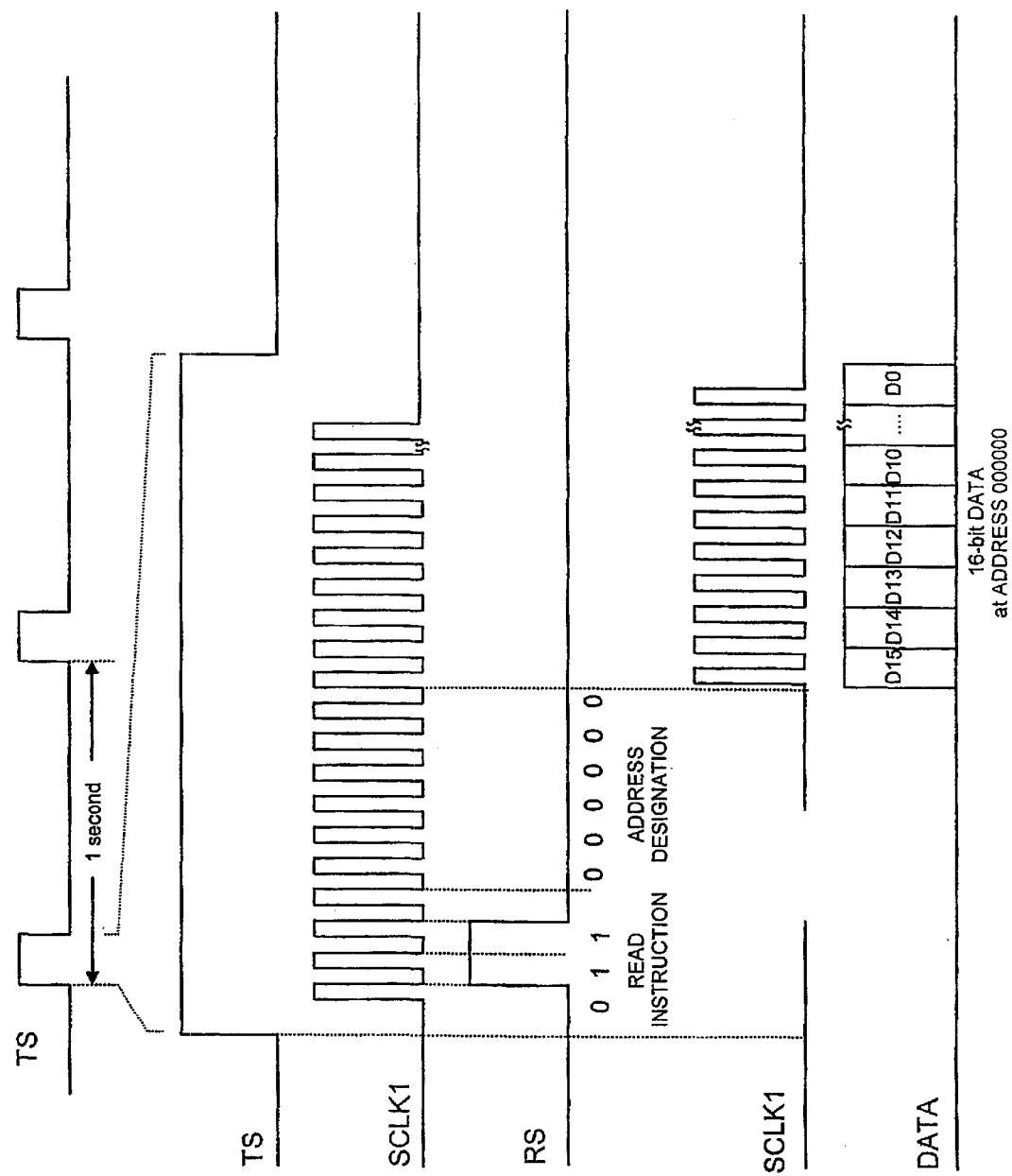
FIG. 9 is a waveform chart illustrating the operation of the memory interface in conjunction with the normal type memory module.

When, on the other hand, the memory 81 is directly connected to the integrated circuit module 10, as shown in FIG. 5, the selector 42 is switched to receive the first clock signal SCLK1 from the memory controller 44. At the same time, the memory controller 44 is activated to send necessary control signals and the first clock signal SCLK1 through read-and-write interfaces 46 to the memory 81, thereby reading the instruction data and transferring the same to the shift-register 60 through the data channel 45 in accordance with the first clock signal SCLK1. In detail, the memory controller 44 generates a timing signal TS periodically, for example, every one second. As shown in FIG. 9, each timing signal TS gives a time frame in which a read signal RS is sent to the memory 81 together with the first clock signal SCLK1 and in which the read data DATA is transmitted together with the first clock signal SCLK1 to the shift-register 50. The read signal RS is composed of a read instruction and an address designation which designates the address of the memory 81 from which the data is to be read. The memory 81, which is an EEPROM, is configured to have a 16-bits data area to store the instruction data at a 6-bits address "000000". The upper 8-bits of the data area are assigned to store the gain value data, while the lower 8-bits are assigned to store the offset value data. Thus, in response to the read instruction "011" followed by the address designation "000000", the 16-bits instruction data is read and is transmitted to the D0 to D15 of the shift-register 60 from which the instruction data is delivered to the respective resistor networks 24 and 34 for the gain adjustment and the offset voltage adjustment. In this manner, the instruction data in the shift-register 50 is updated every 1 second so that, even if the instruction data in the shift-register should be modified into erroneous data by transient noise, the shift-register is continuously supplied with the correct data from the memory for keeping the consistent adjustment and therefore reliable sensor output. The writing of the instruction data can be made with the memory 81 connected to the memory interface 40. For this purpose, the input terminal 41 of the memory interface 40 includes a write enable terminal WR which is connected internally to the read-and-write interfaces 46 and is adapted for connection to an external writing device. When connected, the writing device sends a write signal to the terminal WR to make the R/W interfaces 46 ready for writing the memory 81 and subsequently send the instruction data with an associated clock signal and the control signal to the terminals EV1, EV2, EV3, and DATA to complete the writing of the instruction data in the memory 81.

What is claimed is:

1. A particle sensor which detects the presence of specific particles and provides an output signal indicative of the amount of the particles being detected, said particle sensor comprising:
    a detector proving an output voltage which is proportional to the amount of particles carried on a medium such as the air being detected;
    a gain controller adjusting the output voltage received from the detector to provide an adjusted output voltage, said gain controller including a gain resistor network which gives a variable resistance in order to vary the adjusted output voltage;
    an offset voltage adjustor providing an adjustable offset voltage indicative of a background voltage which is combined with said adjusted output voltage to provide a sensor output which satisfies a predetermined (regulation) relationship between a particle density and the sensor output, said offset voltage adjustor comprising an offset resistor network which gives a variable resistance in order to adjust the offset voltage,
    at least one of the gain resistor network and the offset resistor network comprising a plurality of digitally controllable switches and a plurality of resistors so as to give the variable resistance varying by conduction of a suitable combination of the switches,
    wherein said particle sensor further including:
        memory means which stores an instruction data designating which one or more of the switches are to be made conductive; and
        a memory interface which transfers the instruction data from the memory means to at least one of the gain resistor network and the offset resistor network.

2. The particle sensor as set forth in claim 1, wherein each of the gain resistor network and the offset resistor network comprising a plurality of digitally controllable switches and a plurality of resistors so as to give the variable resistance varying by conduction of a suitable combination of the switches.

3. The particle sensor as set forth in claim 1, wherein said memory interface comprises:
    a memory controller which sends a first clock signal and a read signal for reading the instruction data by means of the first clock signal and delivering the instruction data to at least one of the gain resistor network and the offset resister network,
    a selector having inputs being respectively adapted to receive the first clock signal from the memory controller and a second clock signal and selecting one of the first clock signal and the second clock signal, the second clock signal being supplied from other than the memory controller and being utilized to read the instruction data from the memory means without relying upon the memory controller and to deliver the instruction data to at least one of the gain resistor network and the offset resister network.

4. The particle sensor as set forth in claim 3, wherein said memory means comprises a non-volatile memory storing said instruction data, and a microcomputer which generates the second clock signal for reading the instruction data from the non-volatile memory and delivering the data to at least one of the gain resistor network and the offset resister network, said microcomputer having a function of writing the instruction data.

5. The particle sensor as set forth in claim 4, wherein said memory interface includes a shift-register connected to the microcomputer through a data channel and connected to the selector for receiving the second clock signal in accordance with which the instruction data is transferred from the microcomputer through the data channel to the shift-register,
    said shift-register being connected to deliver the instruction data to the gain resistor network and the offset resistor network.

6. The particle sensor as set forth in claim 5, wherein said instruction data has a structure composed of
    a gain value data having plural bits each designating a conduction state of the corresponding one of the switches included in the gain resistor network,
    a reverse gain value data having reversed bits of the gain value data;
    an offset value data having plural bit each designating a conduction state of the corresponding one of the switches included in the offset resistor network; and
    a reverse offset value data having reversed bits of the off set value data, said memory interface comprising:
        a data validation means which fetches the instruction data from the shift-register to compare the bits of the gain value data with the corresponding reversed bits, and compare the bits of the offset value data with the corresponding reversed bits in order to verify the gain value data and the offset value data, and provides an error signal when any one of the data is not verified,
    said microcomputer acting, in response to the error signal, to retransmit the instruction data from the memory to the shift-register.

7. The particle sensor as set forth in claim 3, wherein said memory means consists of a non-volatile memory storing said instruction data which is transmitted to said memory interface by the memory controller, and
    said instruction data including a gain value data for controlling the switches of the gain resistor network, and an offset value data for controlling the switches of the offset resistor network.

8. The particle sensor as set forth in claim 7, wherein said memory controller fetches the instruction data periodically from the memory for transmission to the switches of the gain resistor network and the offset resistor network.

9. The particle sensor as set forth in claim 3, wherein said memory interface includes a writing interface which accepts a write signal from an external writing device and enables the writing device to write the instruction data in the memory means.

10. A particle sensor which detects the presence of specific particles and provides an output signal indicative of the amount of the particles being detected, said particle sensor comprising:

a detector proving an output voltage which is proportional to the amount of particles on a medium such as the air being detected;

a gain controller adjusting the output voltage received from the photo detector to provide an adjusted output voltage, said gain controller including a gain resistor network which gives a variable resistance in order to vary the adjusted output voltage;

an offset voltage adjustor providing an adjustable offset voltage indicative of a background voltage which is combined with said adjusted output voltage to provide a sensor output which satisfies a predetermined (regulation) relationship between a particle density and the sensor output, said offset voltage adjustor comprising an offset resistor network which gives a variable resistance in order to adjust the offset voltage, at least one of the gain resistor network and the offset resistor network comprising a plurality of digitally controllable switches and a plurality of resistors so as to give the variable resistance varying by conduction of a suitable combination of the switches, wherein said detector further including:

a memory interface having a input terminal adapted for selective connection with a first non-volatile memory through a microcomputer, and directly with a second non-volatile memory, each of said first and second memories storing an instruction data designating which one or more of the switches are to be made conductive, said microcomputer having a function of writing the instruction data in the associated memory, said memory interface comprising:

a memory controller which sends a first clock signal and a read signal for reading from the second memory the instruction data in accordance with the first clock and delivering the instruction data to at least one of the gain resistor network and the offset resister network, a selector adapted to receive the first clock signal from the memory controller and a second clock signal from the microcomputer and to select one of the first clock signal and the second clock signal, the second clock signal being utilized to read the instruction data from the first memory by the microcomputer and to deliver the instruction data to at least one of the gain resistor network and the offset resister network.

11. The particle sensor as set forth in claim 10, wherein said selector is connected to the memory controller so as to activate the memory controller only when the selector is switched for connection of the second memory to the memory interface.

* * * * *